United States Patent [19]

Lindner et al.

[11] 4,416,279

[45] Nov. 22, 1983

[54] CAPILLARY BLOOD SAMPLING DEVICE

[76] Inventors: James A. Lindner, 4316 168th St., Flushing, N.Y. 11358; Roger E. Desroches, 93-10 112th St., Richmond Hill, N.Y. 11418

[21] Appl. No.: 275,218

[22] Filed: Jun. 19, 1981

[51] Int. Cl.³ .............................................. A61B 17/32
[52] U.S. Cl. ................................ 128/314; 128/329 R; 128/770; 206/367
[58] Field of Search ................... 128/763, 770, 329 R, 128/314, 769, 764-766; 83/919, 866; 206/367

[56] References Cited

U.S. PATENT DOCUMENTS 3,030,959 4/1962 Grünert .............................. 128/314
3,358,689 12/1967 Higgins .............................. 206/367

Primary Examiner—Henry J. Recla
Assistant Examiner—Karin M. Reichle
Attorney, Agent, or Firm—S. C. Yuter

[57] ABSTRACT

An improved capillary blood sampling device comprising a longitudinal body having a finger position area at one end and a longitudinal access opening to receive a spring-operated lancet holder. The lancet holder is moved longitudinally by a rotatable operating member at the other end of the body. Rotation of the operating member first withdraws the lancet holder away from the finger position area so that a lancet may be loaded while simultaneously compressing the spring. Further rotation in the same direction releases the lancet holder plunging the lancet point into the finger. When the lancet plunges into the finger the spring is compressed causing almost instant retraction of the lancet point from the finger. The finger position area may comprise a disposable platform. The lancet holder may have a ball socket adapted to receive a ball-based lancet.

13 Claims, 12 Drawing Figures

U.S. Patent  Nov. 22, 1983  Sheet 1 of 3  4,416,279
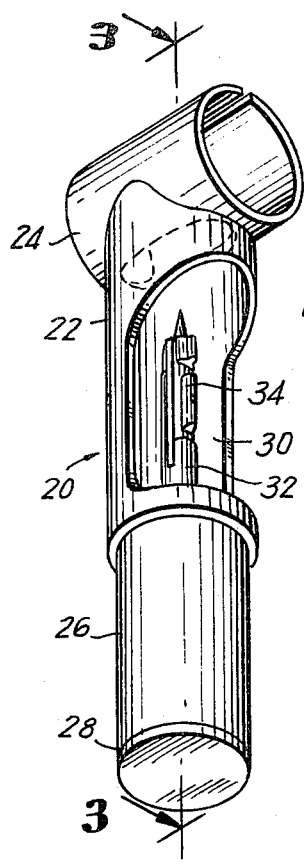
FIG. 1
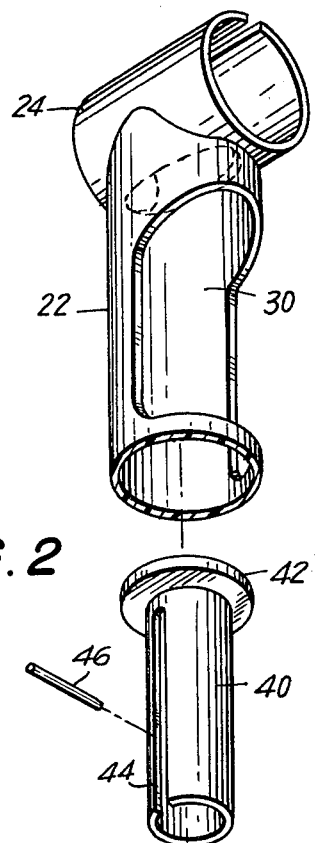
FIG. 2
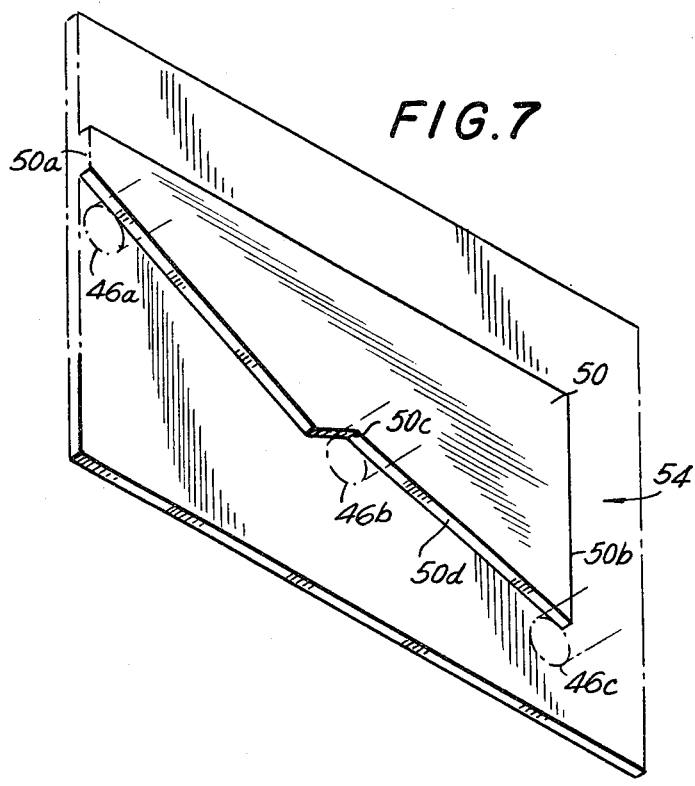
FIG. 7
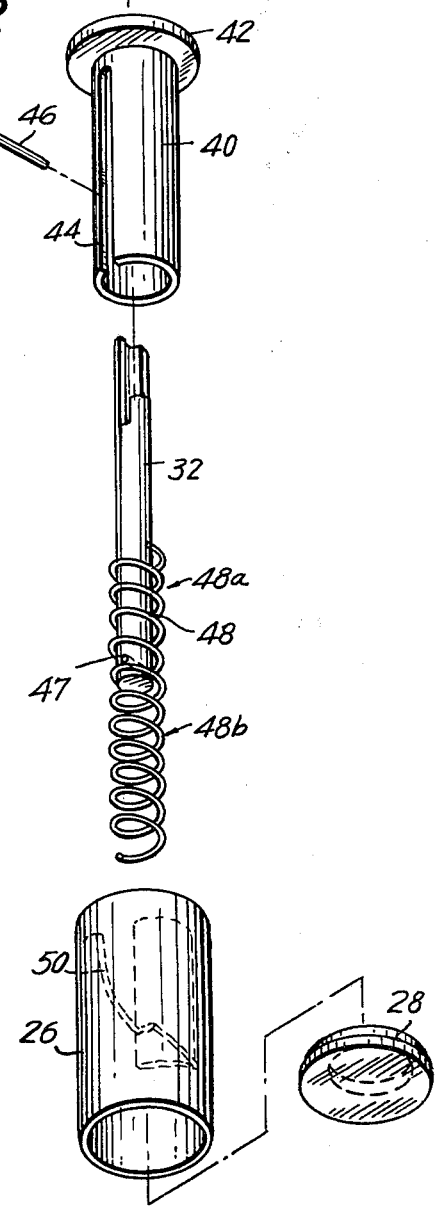

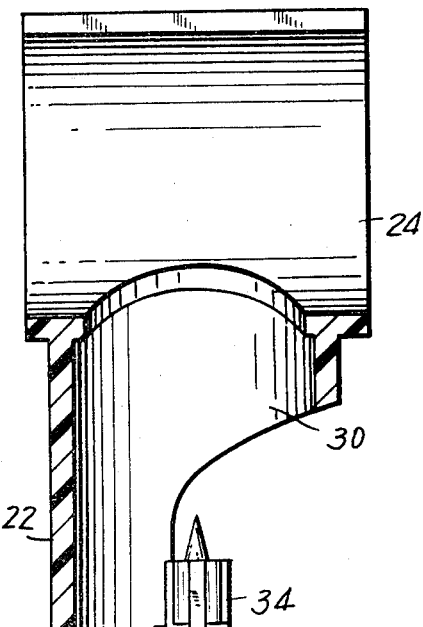
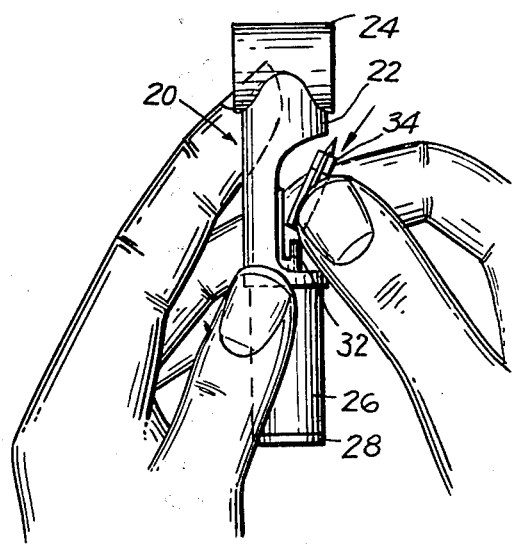
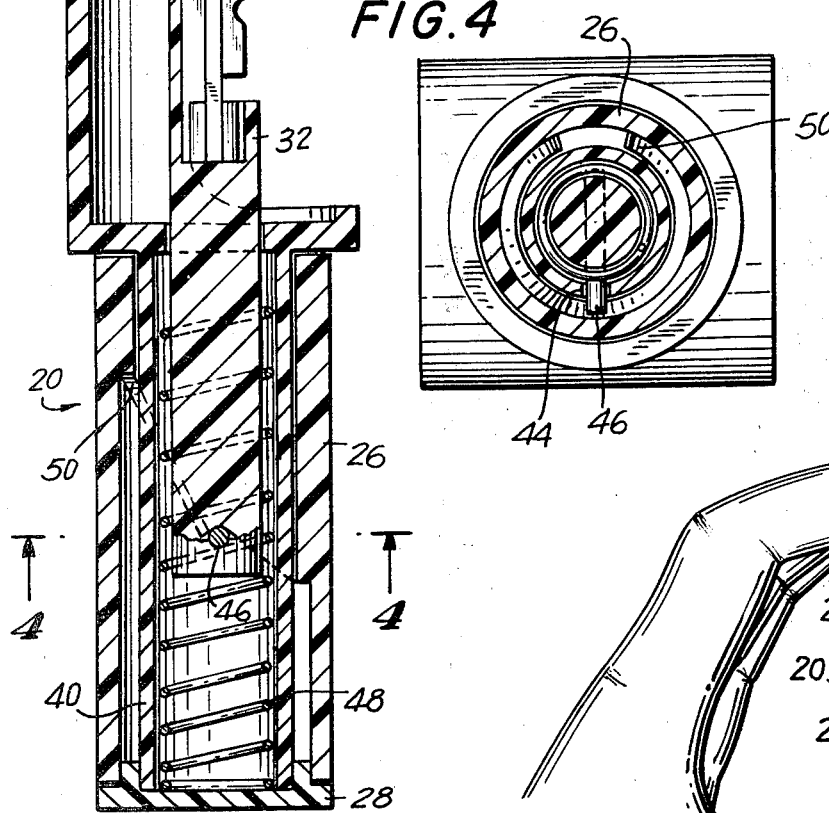
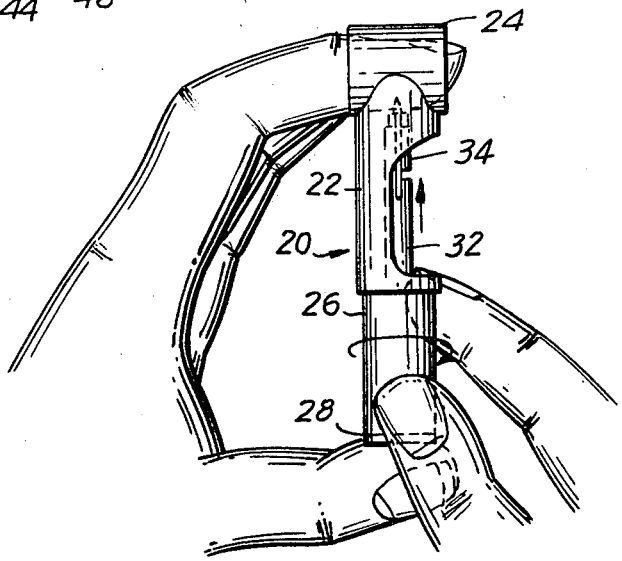

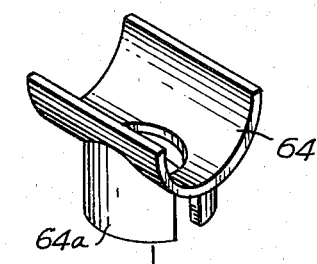
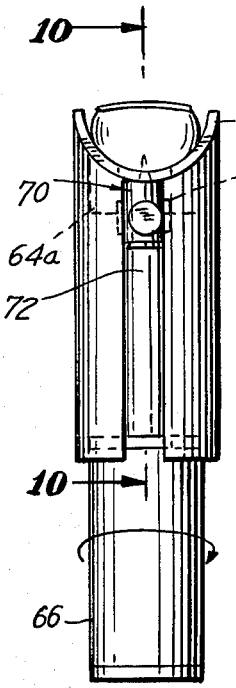
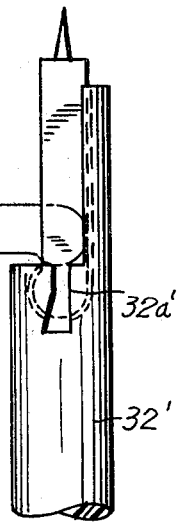
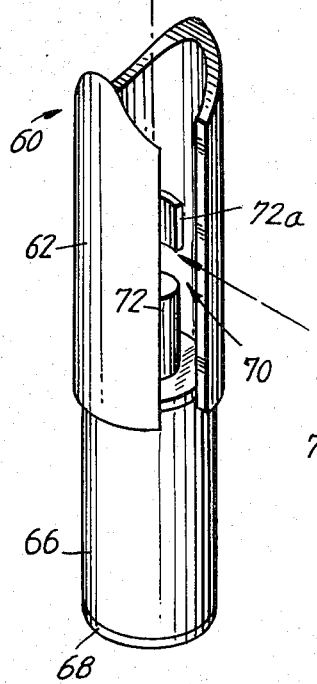
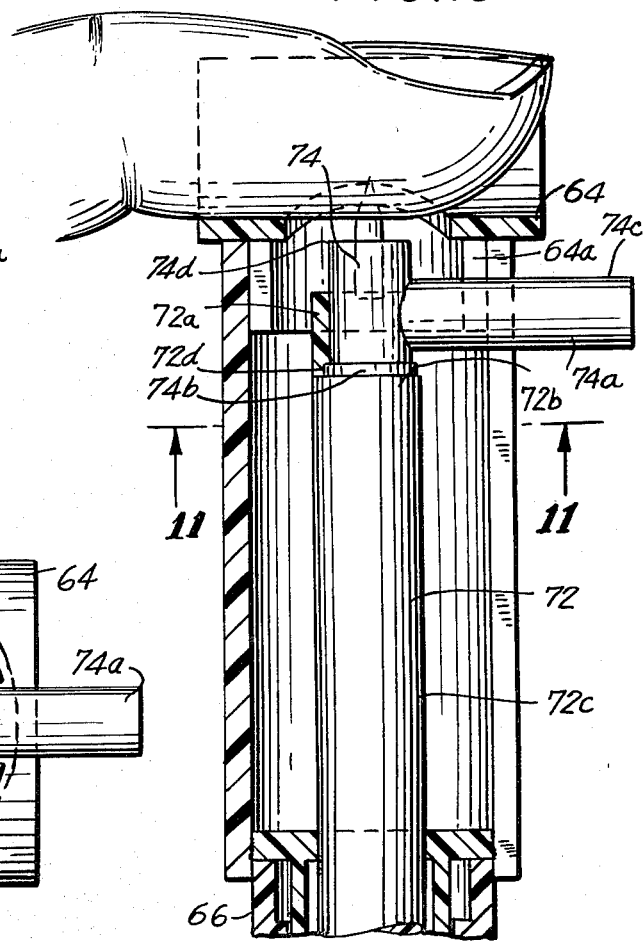
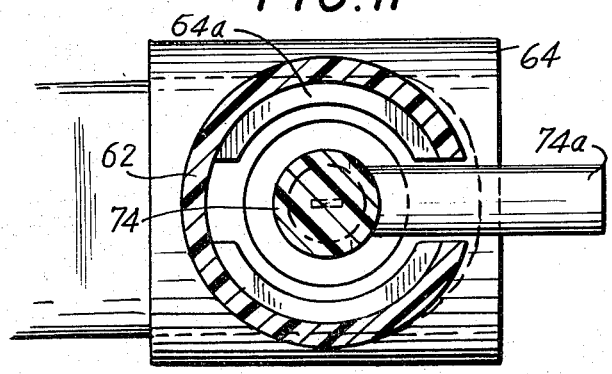

CAPILLARY BLOOD SAMPLING DEVICE

This invention relates to an improved capillary blood sampling device and more particularly to a device for lancing a finger in order to obtain a blood sample for diagnostic purposes.

BACKGROUND OF INVENTION

An increasing number of capillary blood samples are being required for a greater variety of diagnostic tests. A long established technique to obtain a blood sample is to manually jab the finger with a disposable lancet. This procedure is rather crude and painful, requires technical training and, because the jabbing is substantially uncontrolled, sometimes requires more than one jab to obtain a good sample.

PRIOR ART

These objections were substantially overcome with the development and marketing of a capillary blood sampling device called the Autolet, manufactured by Owen Mumford, Ltd., Oxford, England, and distributed in the United States by Ulster Scientific, Inc., Highland, N.Y. The Autolet uses a disposable, sterile lancet (described in U.S. Pat. No. 3,358,689) whose needle is precision ground to make an immediate, easy, blood-flowing incision. The lancet is fitted in a spring loaded arm which is pulled back against a spring and secured by a retaining catch operated by a quick release button. The finger is then gently held against an apertured platform so the pulp of the finger is visible through the hole of the platform. Then the button is actuated releasing the spring loaded arm to traverse a rapid arc and pierce the finger. The lancet is supposed to puncture the tissue very rapidly and cleanly and to a controlled and repeatable depth.

While the Autolet is a major improvement over the jabbing technique, it suffers from a number of problems. Foremost among these problems is the apprehension of the user who anticipates that pain will occur immediately on actuating the release button. Coupled with this apprehension is a tendency to draw the target finger away from the platform so that no, or an insufficient, incision is made—which requires that the device be recocked and employed again, increasing the apprehension of the user.

BRIEF DESCRIPTION OF INVENTION

The general object of this invention is to provide a capillary blood sampling device which is a substantial improvement over the Autolet unit.

A specific object of the invention is to provide an improved capillary blood sampling device which lowers the apprehension of the user and thus is more psychologically acceptable.

Another specific object of the invention is to provide an improved capillary blood sampling device which positively positions the target finger making it difficult to withdraw in anticipation of pain.

Briefly, in accordance with the invention, an improved capillary blood sampling device is provided comprising a longitudinal body having a finger position area at one end and a longitudinal access opening to receive a lancet in a spring-operated lancet holder. The lancet holder is moved longitudinally by a rotatable operating member at the other end of the body. Rotation of the operating member first withdraws the lancet holder away from the finger position area so that a lancet may be loaded while simultaneously compressing the spring. Further rotation in the same direction releases the lancet holder plunging the lancet into the finger.

The device is held between the target finger and the thumb so that positive pressure between the two fingers is required to prevent dropping the device. That maintains the target finger in contact with the finger positioning area and deters anticipatory withdrawal of the target finger.

Since the device is operated by continuously rotating the operating member in the same direction, there is no clear indication when the plunger will be actuated so that apprehension is reduced by the relative suprise of the puncture.

A feature of the invention is almost instant retraction of the lancet after the puncture due to compression of the spring adjacent the finger position area as the lancet holder is propelled against the target finger.

An advantage of the invention is that the lancet is loaded within the body and thus is not capable of accidentally pricking the user (as is the Autolet unit when the lancet is in the cocked and thus exposed position).

Additional objects, features and advantages of the invention will be apparent from the following detailed specification of the invention illustrated by the accompanying drawings wherein:

FIG. 1 is a front perspective view of an improved capillary blood sampling device, in accordance with the first embodiment of the invention, showing the lancet mounted in the lancet holder and pointed at the finger position area, with the rotating operating member beneath the lancet holder.

FIG. 2 is an exploded perspective view of the capillary blood sampling device of FIG. 1 (but without a lancet) showing the dual action spring which both propels the lancet into the finger and immediately retracts it.

FIG. 3 is a side elevational view of the capillary blood sampling device of FIG. 1, partly broken away, showing the spring partially compressed in the lance load position prior to launching the lancet toward the finger.

FIG. 4 is a cross-sectional view of the device along the lines of 4—4 of FIG. 3.

FIG. 5 shows how the lancet is loaded into the lancet holder.

FIG. 6 shows how the device is held between the target finger and thumb of one hand and the operating member is rotated with the other hand to release the spring-loaded lancet holder at some point during rotation.

FIG. 7 is a developed view of the cam, shown in dotted outline in FIG. 2, which functions to retract the spring-loaded lancet holder with rotation of the operating member and then to release the lancet holder driving it toward the target finger.

FIG. 8 is a front perspective exploded view of the improved capillary blood sampling device, in accordance with the preferred embodiment of the invention, which differs from the FIGS. 1-7 embodiment principally in having a disposable platform for the finger positioning area and a snap-in lancet.

FIG. 9 is a front elevational view of the device of FIG. 8 showing the target finger during lancing.

FIG. 10 is a side elevational view taken along the lines 10—10 of FIG. 9, also showing the lancet in the finger puncturing position.

FIG. 11 is a cross-sectional view of the FIG. 8 device taken along the lines 11—11 of FIG. 10 showing the snap-in lancet after insertion.

FIG. 12 is a side elevational view of a portion of a lancet holder and a lancet in accordance with a modified embodiment of the invention.

Referring to FIG. 1, the improved capillary blood sampling device 20 comprises a body cylinder 22 having a finger position member 24 at one end, an operating cylinder 26 at the other end together with end cap 28. The body cylinder 22 has a longitudinal access opening 30 which has a lancet holder plunger 32 adapted to receive and hold a lancet 34. The operating cylinder 26 is rotated to retract the lancet holder plunger 32 so that a lancet 34 can be inserted (FIG. 5). Then the target finger is inserted into the finger position member 24 (FIG. 6) and the device 20 held between the target finger and the thumb of the same hand while the operating cylinder is rotated to a point which releases the lancet holder plunger 32 to drive the lancet 34 into the pulp of the target finger to a sufficient and controlled depth to lance the finger and produce a suitable sample of blood for diagnostic purposes. Alternatively, the device 20 may be held between the thumb as the target finger and another finger.

FIG. 2 shows the internal construction of the capillary blood sampling device 20. Slotted guide 40 is fixedly positioned in the bottom opening of body cylinder 22 via connecting member 42. End cap 28 is connected to the bottom of slotted guide 40 (FIG. 3). Slotted guide 40 (FIG. 2) has a single slot 44 which receives and guides follower pin 46. Lancet holder plunger 32 is encircled by spring 48 and, together with spring 48, is slidably positioned within slotted guide 40.

Follower pin 46 passes through hole 47 in lancet holder plunger 32 and separates spring 48 into upper turns 48a and lower turns 48b. Lower turns 48b are compressed when the lancet holder plunger 32 is retracted to load a lancet 34.

The lower turns 48b are compressed as the follower pin 46 is moved longitudinally away from the finger position member 24 by the internal cam 50 of the operating cylinder 26. FIG. 3 shows the follower pin 46 at the loading position of the cam 50 after movement of the follower pin 46 downward with rotation of operating cylinder 26 in the clockwise direction.

FIG. 7 shows the cam 50 in a developed view. The vertical separation 54 between the two end edges 50a and 50b of the cam 50 is the starting point for the follower pin 46 because it is in the vertical separation 54 that the lancet holder plunger 32 is released to drive toward the target finger. Further rotation of the operating cylinder 26 first positions the follower pin at point 46a because spring 48 when uncompressed positions pin 46 in vertical alignment with point 46a. Still further rotation moves the follower pin 46 to position 46b where the pin snaps into position in the cam angle 50c. This is the loading position for the device 20; that is, the lancet holder plunger 32 is then retracted to the position shown in FIG. 5 for the loading of a lancet 34. Further rotation of the operating cylinder 26 (FIG. 6) moves the follower pin along cam edge 50d (FIG. 7) to the maximum retraction position 46c, further compressing the lower turns 48b of the spring 48 (FIG. 2). Edge 50d has a slight inward bevel to prevent binding.

The next rotation of the operating cylinder 26 moves the follower pin 46 into the vertical separation 54 whereupon the follower pin 46 is released and compressed lower turns 48b propel the lancet holder plunger 32 toward the target finger to make the incision. Upper turns 48a are compressed when the released lancet holder plunger presses the lancet 34 against the target finger causing the lancet to immediately retract after the incision.

Since the user does not know exactly when the follower pin 46 will move into the vertical separation 54 to release the lancet holder plunger 32, the incision usually comes as some surprise thus reducing apprehension. Moreover, since the operating cylinder 26 is rotated with one hand while the capillary sampling device 20 is held between the target finger and the thumb of the other hand (FIG. 6), the target finger is kept pressed against the bottom surface of the finger position member 24 facilitating an incision to the proper *minimum* depth.

FIGS. 8–11 show the preferred embodiment of the improved capillary sampling device invention. Device 60 (FIG. 8) comprises a body cylinder 62 having a disposable finger position platform 64 at one end, an operating cylinder 66 at the other end and an end cap 68. The body cylinder 62 has a narrow longitudinal access opening 70 in which a lancet holder 72 is adapted to receive and hold a lancet 74. The width of the access opening 70 is slightly larger than the maximum width of the lancet 74. The operating cylinder 66 is rotated to retract the lancet holder plunger 72 so that a lancet 74 can be snapped into the holder 72 through the access opening 70. Loading of the lancet 74 is facilitated by stub 74a. Flange 74b of stub 74a fits into recess 72d of holder plunger 72 to locate lance 74 in lancet receiver 72a. Otherwise capillary sampling device 60 operates substantially the same as capillary sampling device 20 shown in FIGS. 1–7.

Disposable finger position platform 64 has a collar extension 64a which plugs into the upper opening end of body cylinder 62. Platform 64 may be unplugged and discarded when the capillary sampling device 60 is to be used by another person. In that case a new and sterile platform 64 is plugged into body cylinder 62. Sterile platform 64, alternatively, may be shaped to be applied against an infant's heel.

Since longitudinal access opening 70 is quite narrow, the loaded lancet 74 is almost completely surrounded so that no accidental pricking can occur.

FIG. 10 shows the detailed construction of the lancet holder plunger 72. It comprises the lancet receiver 72a which resiliently receives the lancet 74 and snaps around it to hold it in position. The lancet propelling member 72b propels the lancet 74 toward the finger. The lancet body 72c corresponds to the lower portion of the lancet holder plunger 32 in FIG. 2.

The distance between the top 74c (FIG. 10) of stub 74a and the top 74d of the plastic portion of lancet 74 may be employed to control the depth of penetration of the lancet needle by top 74c being stopped by the bottom surface of sterile platform 64.

The balance of the lower construction of the capillary sampling device 60 of FIGS. 8–11 is the same as the lower construction of the capillary sampling device 20 of FIGS. 1–7. The retraction and propelling of the lancet holder plungers 32 and 72 operate in the same manner.

FIG. 12 shows a modified embodiment of the invention shown in FIG. 3 with lancet holder plunger 32 of FIG. 3 modified as lancet holder plunger 32' (FIG. 12) to provide a resilient socket receptacle 32a' in which a ball-based lancet 34' (shown in dotted outline) is plugged. The advantage of this modification of the invention is that the lancet 34' can be loaded into the lancet holder plunger 32' at an angle and then swiveled to a vertical position as shown in FIG. 3 in preparation for retraction and subsequent propelling into the target finger with rotation of the operating cylinder 26.

It should be understood that various parts of the capillary sampling devices 20 and 60 could be molded together and that the preferred material for these devices is buterate or similar plastic, except for metal spring 48.

What is claimed is:

1. An improved capillary blood sampling device comprising:
    (a) a longitudinal hollow tubular body having an access opening in the side to receive a lancet and open opposite ends;
    (b) a finger position area defined at one of said open ends of said longitudinal body;
    (c) a rotational operating member rotationally connected at the other of said open ends of said longitudinal body;
    (d) a lancet holder positioned concentrically within said longitudinal body and said rotational operating member and adapted to be moved between a loading position and a released position;
    (e) spring means within said rotational operating member coupled to said lancet holder and adapted to be compressed by said lancet holder when said lancet holder is moved away from said finger position area toward said loading position;
    (f) said rotational operating member having spring operation means adapted to move said lancet holder toward said loading position to compress said spring means in response to rotation thereof and also adapted to release said lancet holder for movement toward said released position in response to further rotation thereof;
    (g) whereby said lancet holder is responsive to rotation of said rotational operating member to move away from said finger position area and compress said spring means to permit loading of a lancet in said lancet holder and responsive to
    (h) further rotation of said rotational operating member to release said lancet holder to be propelled toward said finger position area by said spring means.

2. The improved capillary blood sampling device of claim 1 further comprising second spring means within said rotational operating member and coupled to said lancet holder which is compressed when the lancet strikes the finger and rapidly withdraws the lancet from the finger.

3. The improved capillary blood sampling device of claim 2 further comprising:
    (i) a slotted guide cylinder connected to said other end of said longitudinal body and encircling said lancet holder and comprising a longitudinal slot;
    (j) said spring means and said second spring means comprising different portions of a plurality of turns of a coil spring positioned within said slotted guide cylinder and encircling said lancet holder;
    (k) a cam follower pin passing orthogonally through said longitudinal slot of said slotted guide cylinder, turns of said coil spring and said lancet holder;
    (l) said spring operation means being connected to said rotational operating member and comprising a cam member mounted on the inside surface of said rotational operating member and engaging said cam follower pin.

4. The improved capillary blood sampling device of claim 1 wherein said finger position area comprises a disposable platform.

5. The improved capillary blood sampling device of claim 1 or claim 2 wherein said access opening in said longitudinal body has a width larger than the width of a lancet adapted to be loaded in said lancet holder and said lancet holder has a lancet receiver into which a lancet may be snapped.

6. The improved capillary blood sampling device of claim 5 further comprising a lancet and wherein said lancet has an orthogonal stub adapted to be grasped for snapping said lancet into said lancet receiver.

7. The improved capillary blood sampling device of claim 6 wherein the width of said access opening is slightly larger than the width of said lancet.

8. The improved capillary blood sampling device of claim 3 further comprising an end cap mounted at the outer end of said operating member so that the device can be grasped between a target finger and thumb of one hand and the operating member rotated with the other hand.

9. An improved capillary blood sampling device comprising:
    (a) a hollow body cylinder having an opening at each end with an orthogonal finger positioning area at one end and a longitudinal access opening between said finger positioning area and the other end;
    (b) a guide cylinder connected to and extending longitudinally from said other end of said body cylinder and having a longitudinal slot;
    (c) a lancet holding plunger slidably positioned within said guide cylinder and having a lancet receptacle at the end nearest said finger positioning area adapted to hold a lancet with its pointed end aimed at said finger positioning area;
    (d) a coil spring having a plurality of turns encircling said lancet holding plunger;
    (e) a pin positioned orthogonally in said lancet holding plunger and extending between turns of said coil spring through the slot of said guide cylinder;
    (f) an operating cylinder rotationally connected to said other end of said body cylinder and encircling said guide cylinder;
    (g) said operating cylinder having an integral pin guide which engages said pin whereby, as said operating cylinder is rotated in one direction:
        (1) said lancet holding plunger is moved away from said finger positioning area compressing turns of said coil spring and permitting the loading of a lancet into said lancet receptacle via the longitudinal access opening of said body cylinder,
        (2) said turns of said coil spring are compressed still further, and
        (3) said lancet holding plunger is released propelling a lancet toward a finger at the finger position area to lance the finger and obtain a small capillary blood sample.

10. The improved capillary blood sampling device of claim 9 wherein the section of the plurality of turns of said coil spring on the side of said pin near to said finger positioning area is momentarily compressed against the end of said slotted guide cylinder adjacent to said finger position area causing the pointed end of the lancet to immediately withdraw from the lanced finger.

11. The improved capillary blood sampling device of claim 9 further comprising a cylinder end cap rotationally mounted at the other end of said operating cylinder so that the device can be grasped between the target finger and thumb of one hand and said operating cylinder rotated with the other hand.

12. The improved capillary blood sampling device of claim 11 wherein the turns of said coil spring between the pin and the outer end of said operating cylinder are compressed against said end cap during rotation of said operating cylinder.

13. The improved capillary blood sampling device of claim 9 wherein said finger positioning area is a disposable platform.

* * * * *